(12) United States Patent
Toscano et al.

(10) Patent No.: US 9,676,708 B2
(45) Date of Patent: Jun. 13, 2017

(54) CONTROLLED HNO RELEASE THROUGH INTRAMOLECULAR CYCLIZATION-ELIMINATION

(71) Applicant: The Johns Hopkins University, Baltimore, MD (US)

(72) Inventors: John P. Toscano, Glen Arm, MD (US); Art D. Sutton, Mount Pleasant, WI (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/439,800

(22) PCT Filed: Oct. 30, 2013

(86) PCT No.: PCT/US2013/067558
§ 371 (c)(1),
(2) Date: Apr. 30, 2015

(87) PCT Pub. No.: WO2014/070919
PCT Pub. Date: May 8, 2014

(65) Prior Publication Data
US 2015/0291519 A1    Oct. 15, 2015

Related U.S. Application Data

(60) Provisional application No. 61/721,298, filed on Nov. 1, 2012.

(51) Int. Cl.
*C07C 311/48* (2006.01)
*A61K 31/4152* (2006.01)
*A61K 31/27* (2006.01)
*A61K 45/06* (2006.01)
*A61K 31/265* (2006.01)

(52) U.S. Cl.
CPC .......... *C07C 311/48* (2013.01); *A61K 31/265* (2013.01); *A61K 31/27* (2013.01); *A61K 31/4152* (2013.01); *A61K 45/06* (2013.01)

(58) Field of Classification Search
CPC .................................................... C07C 311/48
See application file for complete search history.

(56) References Cited

U.S. PATENT DOCUMENTS 8,030,356 B2    10/2011  Toscano et al.
2011/0144067 A1*  6/2011  Toscano ............... C07C 311/48
                                                    514/157

OTHER PUBLICATIONS

Chemical Abstract Service (CAS) STN Registry Database No. 1346779-36-9 [entered STN: Dec. 1, 2011].*
International Search Reported dated Feb. 4, 2012 in International Patent Application No. PCT/US2013/067558.
Written Opinion of the International Searching Authority dated Feb. 4, 2014 in International Patent Application No. PCT/US213/067558.

* cited by examiner

*Primary Examiner* — Michael Barker
*Assistant Examiner* — Amanda L Aguirre
(74) *Attorney, Agent, or Firm* — Byrne Poh LLP; Nina R. Horan

(57) ABSTRACT

Protected HNO donors designed to undergo non-enzymatic release at neutral pH via an intramolecular cyclization-elimination are disclosed. The rate of cyclization, and therefore HNO release, can be controlled by substituents and chain length. Thus, biologically useful HNO donors having tunable HNO release rates are provided.

18 Claims, No Drawings

CONTROLLED HNO RELEASE THROUGH INTRAMOLECULAR CYCLIZATION-ELIMINATION

CROSS-REFERENCE TO RELATED APPLICATIONS

This application is a national stage of International Application No. PCT/US2013/067558, filed Oct. 30, 2013, which claims the benefit under 35 U.S.C. §119(e) of U.S. Provisional Patent Application No. 61/721,298, filed Nov. 1, 2012, the contents of all of which are incorporated herein by reference.

FEDERALLY SPONSORED RESEARCH OR DEVELOPMENT

This invention was made in part with United States Government support under CHE-0911305 awarded by the National Science Foundation (NSF). The U.S. Government has certain rights in the invention.

BACKGROUND

Nitroxyl (HNO) has been shown to have positive cardiovascular effects in in vitro and in vivo models of failing hearts. Due to its inherent reactivity, however, HNO must be generated in situ through the use of prodrugs. But beyond Angeli's salt ($Na_2N_2O_3$), derivatives of Piloty's acid ($RSO_2NR'OR''$), and acyloxy nitroso compounds ($AcONOR_2$), very few physiologically useful HNO donors exist. To further elucidate and exploit the physiological effects of HNO, more classes of donor compounds need to be developed.

SUMMARY

In some aspects, the presently disclosed subject matter provides compounds that are capable of undergoing intramolecular cyclization-elimination at a neutral pH under physiological conditions to non-enzymatically release or donate HNO.

In certain aspects, the presently disclosed subject matter provides a compound of formula (I):

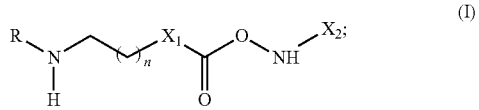
(I)

wherein: n is an integer selected from the group consisting of 1, 2, or 3; $X_1$ is selected from the group consisting of O and $NR_1$; R and $R_1$ are each independently selected from the group consisting of H, unsubstituted or substituted linear or branched alkyl, and unsubstituted or substituted aryl; $X_2$ is a leaving group selected from the group consisting of halogen and L-Y, wherein L is a bond, —$SO_2$—, or –O—, and Y is W (as defined herein below), alkyl or monocyclic, bicyclic or tricyclic cycloalkyl, heterocycloalkyl, aryl, or heteroaryl, each of which are unsubstituted or substituted with one or more substituent groups, and pharmaceutically acceptable salts and hydrates thereof.

In particular aspects, the compound of formula (I) has the following structure:

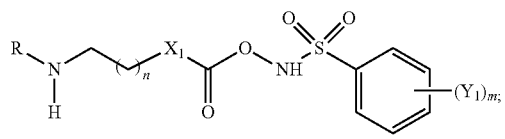

wherein: m is an integer selected from the group consisting of 0, 1, 2, 3, 4, and 5; and each $Y_1$ is independently selected from the group consisting of substituted or unsubstituted linear or branched alkyl, alkoxyl, perhaloalkyl, hydroxyl, hydroxyalkyl, alkylsulfonyl, alkylsulfanyl, alkylsulfinyl, N-hydroxylsulfonamidyl, carboxyl, carbonyl, carbamoyl, alkylcarbamoyl, halogen, amino, dialkylamino, cycloalkoxyl, cycloalkylsulfanyl, arylsulfanyl, arylsulfinyl, nitro, cyano, nitrile, amide, haloalkyl, substituted or unsubstituted heterocycloalkyl, substituted or unsubstituted aryl, aryloxyl, substituted aryloxyl, cycloalkyl, aralkyloxyl, —$SO_3H$, and acyl.

In other aspects, the presently disclosed subject matter provides a method for modulating an in vivo nitroxyl level in a subject in need thereof, the method comprising administering to the subject one or more presently disclosed compounds of formula (I), or a pharmaceutically acceptable salt or hydrate thereof, in an amount effective to modulate the in vivo nitroxyl level.

The some aspects, the presently disclosed compounds of formula (I) can be used for treating failing hearts and can be administered intravenously, orally, or transdermally. Accordingly, in some aspects, the presently disclosed subject matter provides a method for treating, preventing, or delaying the onset or development of a disease or condition that is responsive to nitroxyl therapy, the method comprising administering to a subject in need thereof a therapeutically effective amount of one or more presently disclosed compounds of formula (I) disclosed immediately hereinabove, or a pharmaceutically acceptable salt or hydrate thereof. In particular aspects, the disease or condition treated by the presently disclosed methods is selected from the group consisting of a cardiovascular disease, congestive heart failure, and myocardial ischemia/reperfusion injury.

In certain aspects, the presently disclosed method of treatment further comprises administering to the subject in combination with one or more presently compounds a second therapeutic agent selected from the group consisting of an angiotensin I-converting enzyme (ACE) inhibitor, an alpha-adrenergic blocker, a central adrenergic inhibitor, a beta-adrenergic blocker, an angiotensin II receptor blocker, a calcium channel blocker, a vasodilator, a phosphodiesterase (PDE) inhibitor, an HMG-CoA reductase inhibitor, a cholesterol-lowering agent, an antiarrhythmic agent, a digitalis drug, a nitrate, a diuretic, an anticoagulant, an antiplatelet agent, a thrombolytic agent, an antioxidant, and combinations thereof.

In further aspects, the presently disclosed subject matter provides a pharmaceutical composition comprising one or more presently disclosed compounds of formula (I), or a pharmaceutically acceptable salt or hydrate thereof, and a pharmaceutically acceptable carrier.

In yet further aspects, the presently disclosed subject matter provides a kit comprising one or more presently disclosed compounds of formula (I), or a pharmaceutically acceptable salt or hydrate thereof, wherein the kit further comprises instructions for use in treating a disease or condition that is responsive to nitroxyl therapy.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter now will be described more fully hereinafter with reference to the accompanying Examples, in which some, but not all embodiments of the presently disclosed subject matter are given. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples. Therefore, it is to be understood that the presently disclosed subject matter is not to be limited to the specific embodiments disclosed and that modifications and other embodiments are intended to be included within the scope of the appended claims.

I. CONTROLLED HNO RELEASE THROUGH INTRAMOLECULAR CYCLIZATION-ELIMINATION

Intramolecular cyclization-elimination with spacer molecules is a commonly used drug release strategy. The intramolecular cyclization-elimination pathway has been demonstrated in prodrugs of alcohols and phenols. Saari, W. S., et al., *J. Med. Chem.* 1990, 33, 97-101; Thomsen, K. F., et al., *Int. J. Pharm.* 1994, 112, 143-152. This strategy involves the conjugation of the desired alcohol or phenol to an alkylamine spacer through either a carbamate or a carbonate bond. Id. In solution, the alkylamine cyclizes and releases the alcohol or phenol (Scheme 1). The rates of cyclization and release are dictated by the substituents (i.e., "R" groups) on both the trigger nitrogen and the carbamate nitrogen. Id.

Scheme 1. Phenols released via intramolecular cyclization-elimination.

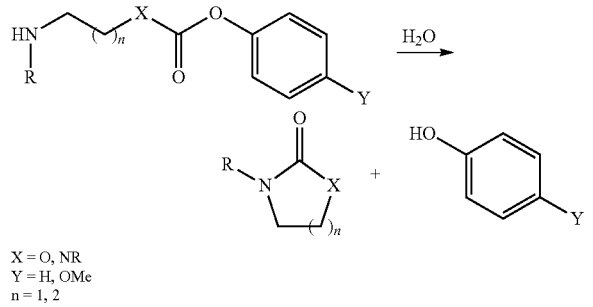

X = O, NR
Y = H, OMe
n = 1, 2

In some embodiments, the presently disclosed subject matter provides Piloty's acid (PA) and N-hydroxy-2-bromobenzenesulfonamide (2BrPA) conjugated to alkylamine spacers as HNO donors (Scheme 2). The release of PA from benzenesulfonamidyl-alkylamino alkylcarbamate hydrochlorides 1 and the release of 2BrPA from 2-bromo-benzenesulfonamidyl-alkylamino alkylcarbonate hydrochlorides 2 can be tuned by modifications to the alkylamine R-substituent group and the length of the spacer (n) (Scheme 2).

Scheme 2. Conjugation of PA and 2BrPA with alkylamine spacers to generate benzenesulfonamidyl-alkylamino alkylcarbamate hydrochlorides 1 and 2-bromo-benzenesulfonamidyl-alkylamino alkylcarbonate hydrochlorides 2.

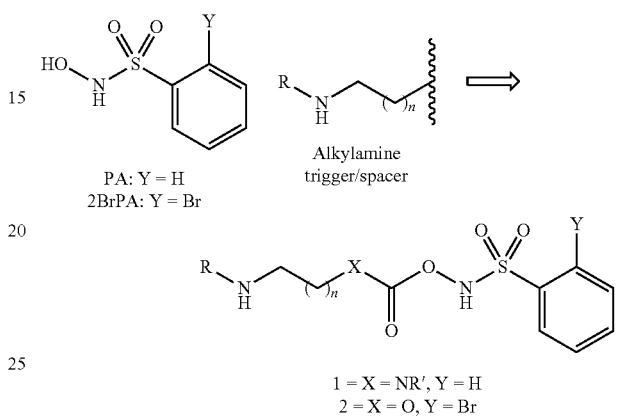

PA: Y = H
2BrPA: Y = Br

Alkylamine trigger/spacer

1 = X = NR', Y = H
2 = X = O, Y = Br

Benzenesulfonamidyl-Alkylamino Ethyl Carbamate Hydrochlorides 1

In representative embodiments, PA/carbamate conjugates 1 were synthesized and evaluated to determine if the use of spacers with PA derivatives was viable. In such embodiments, PA was used as a test molecule due to the availability of the starting reagents. The use of PA as the model drug to be released was advantageous for decomposition analysis. Because of its long half-life (>1 hour), PA accumulates and is observed during the decomposition of 1 by HPLC (Table 1).

TABLE 1

Rates of PA release from benzenesulfonamidyl-alkylamino ethyl carbamate hydrochlorides 1

| Cmpd | R | R' | $t_{1/2}{}^a$ | PA obs.$^a$ |
|---|---|---|---|---|
| 1a | Me | Me | 3 min | Yes |
| 1b | Bnz | Me | 7 min | Yes |
| 1c | iPr | Me | 29 min | Yes |
| 1d | Ph | Me | B | B |
| 1e | Me | Et | 5 min | Yes |
| 1f | Me | Bnz | C | C |
| 1g | Me | sBu | D | D |

Donor compounds were incubated at 37° C. in PBS (pH 7.4).
$^a$Determined by HPLC (SEM ± 5%; n = 3).
$^b$By product interfered with analysis.
$^c$Stable over 13 hours.
$^d$Stable over 24 hours.

The data from Table 1 indicate the viability of using spacers as a controlled release strategy for PA derivatives.

Derivatives 1a, 1b, 1c, and 1e all released PA. The steric environment (R) of the trigger amine influenced the half-life. For example, the half-life of 1c (R is iso-propyl) is 29 minutes, whereas the half-life of 1a (R is methyl) is 3 minutes (Table 1).

The steric environment (R') of the carbamate bond also influences the cyclization rate. The increased size of R' of 1f (R' is benzyl) and 1g (R' is sec-butyl) render them essentially stable compared to 1a (R' is methyl) and 1e (R' is ethyl).

Without wishing to be bound to any one particular theory, modifications to the alkyl group (R) of the trigger amine are thought to allow more control of the rate of cyclization and elimination of PA as compared to (R') on the carbamate nitrogen. Since the carbamate spacers were difficult to synthesize and purify, the attention was focused on carbonate linked (X=O) analogues 2 instead.

Benzenesulfonamidyl-Alkylamino-Alkylcarbonate Hydrochlorides 2

The donor 2BrPA produces HNO in high yield at pH 7.4 with a single defined half-life of approximately 2 minutes. See U.S. Pat. No. 8,030,356, to Toscano et al., which is incorporated herein by reference in its entirety. Changing (R) on the trigger amine or the spacer length (n) in 2 makes it possible to tune the effective HNO production rate through controlled 2BrPA release (Table 2). Donors 2, with release rates slower than the half-life of 2BrPA, produce HNO at the rate of cyclization. The decomposition products, rates, and HNO production were analyzed and compared to 2BrPA (Table 2).

TABLE 2

Decomposition of 2-bromo-benzenesulfonamidyl-alkylamino carbonates 2

| Cmpd | R | N | $t_{1/2}$ | % HNO[a] |
|---|---|---|---|---|
| 2a | Me | 1 | 54 sec[b] | 93 |
| 2b | Bnz | 1 | 60 sec[b] | 99 |
| 2c | iPr | 1 | 47 sec[b] | 97 |
| 2d | tBu | 1 | 47 min[c] | 64 |
| 2e | Ph | 1 | 22 min[c] | 91 |
| 2f | 4-OMe—Ph | 1 | 50 sec[b] | 93 |
| 2g | 4-Cl—Ph | 1 | 50 min[c] | 69 |
| 2h | iPr | 2 | ~18 hour[c] | 30 |

[a]Donor compounds were incubated at 37° C. in PBS (pH 7.4). HNO yields were determined from $N_2O$ headspace analysis using a calibration standard following complete decomposition (SEM 5%; n = 3). HNO yields are reported in comparison to 2BrPA HNO was confirmed as the source of $N_2O$ by complete quenching with added glutathione.
[b]Determined by UV/vis (SEM ± 5%; n = 3).
[c]Determined by HPLC (SEM ± 5%; n = 3).

Amine Steric Environment and its Effect on the Release Rate

The data in Table 2 indicate that the aliphatic derivatives 2a, 2b, and 2c containing an alkylamine trigger rapidly release 2BrPA when incubated in PBS buffer. The half-lives of 2a, 2b, and 2c were each less than 1 minute. This observation is consistent with alkylamines being good nucleophiles and the ready formation of five-membered rings (step (a), Scheme 3). The use of tert-butylamine in 2d hindered the cyclization (Table 3). Derivative 2 has a half life of 47 minutes, which is significantly longer than 2a, 2b, and 2c. The decomposition of 2d yields only 64% of expected amount of HNO from 2BrPA (Table 2).

Byproduct Ring Size and its Effect on Release Rate

When the spacer is extended by one methylene, the half-life also increased significantly. The N-isopropyl-aminopropyl derivative 2h has a half-life of 18 hours compared to its shorter N-isopropyl-aminoethyl analog 2c, which has a half-life of approximately 0.8 minutes (Table 2). The difference in release kinetics also was consistent based on the size of the ring formed (Scheme 3). It is possible to modify the half-life of 2h with increased branching on the alkyl spacer. Increased branching could bias a conformation in which the trigger amine in closer to the carbonate link. This conformation would result in faster release rates compared to 2h. Similarly the HNO yield of 2h was only 30% of that observed for 2BrPA.

Scheme 3. Expected decomposition of 2c and 2h to produce (a) 5-membered byproduct 3 and (b) 6-membered byproduct 4.

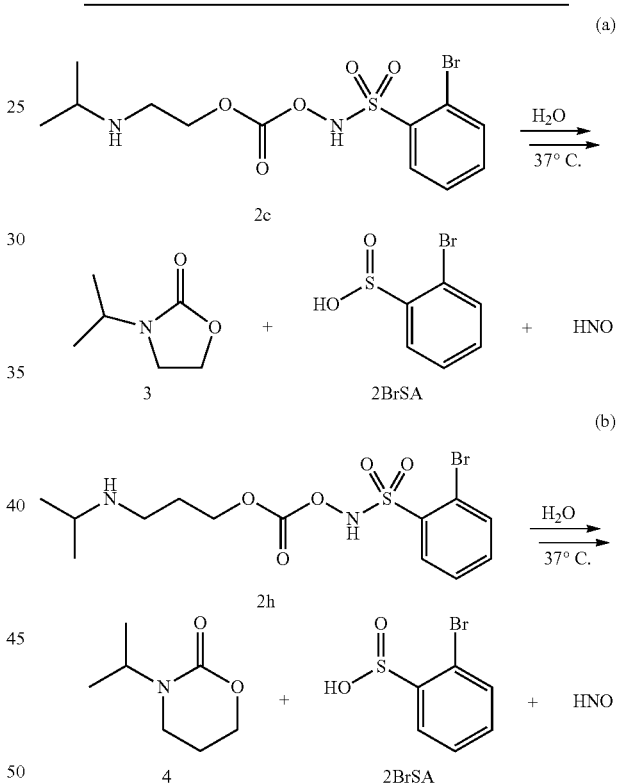

Amine Nucleophilicity and its Effect on the Release Rate

In addition to changing the sterics of the trigger amine (R) and the length (n), of the spacer (see Scheme 2), the nucleophilicity of the amine trigger was investigated. The phenyl derivative 2e has a half-life of 22 minutes, which is significantly longer than its alkylamine counterparts 2a, 2b, 2c, excluding 2d (Table 2). Alkylamines are more nucleophilic relative to arylamines Comparison of the arylamine triggers in 2e, 2f, and 2g shows half-lives of 22 minutes, 0.8 minutes, and 50 minutes respectively (Table 2). Activated ring systems, such as 2f, are expected to accelerate the release of 2BrPA relative to the unsubstituted 2e, whereas deactivated systems like 2g are expected to slow down the release. This observation demonstrates that release of 2BrPA can be tuned based on the nucleophilicity of the amine trigger. It also should be noted that 2g yielded only 69% of the HNO produced from 2BrPA.

The decomposition of derivatives 1 and 2 were monitored by HPLC analysis. In each case, a clean decomposition was observed from the derivative to either PA or 2-bromobenzenesulfinic acid (2BrSA), the byproduct of 2BrPA decomposition. When 2d, 2g, and 2h were evaluated for HNO production compared to 2BrPA, the yields were significantly lower (Table 2). Closer monitoring of 2d by NMR experiments suggests the presence of other pathways not observable by HPLC (Scheme 4).

Scheme 4. Decomposition products of 2-bromo-benzenesulfonamidyl-(tert-butylamino) ethyl carbonate hydrochloride 2d

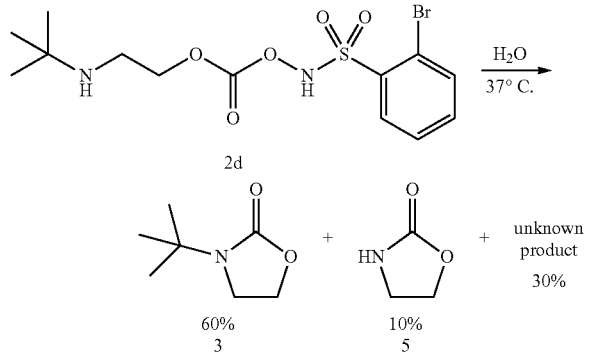

The cyclized byproduct 3, expected from an HNO forming pathway, from 2d, formed in approximately 60% yield (Scheme 4). The yield of 3 is consistent with the yield of HNO detected (64%) (Table 2). The cyclized product 5 also was identified and formed in approximately 10% yield. Another byproduct formed in approximately 30% yield.

Representative Embodiments of Compounds of Formula (I)

The presently disclosed subject matter provides compounds of formula (I), which are capable of undergoing intramolecular cyclization-elimination at a neutral pH under physiological conditions to non-enzymatically release or donate HNO. Accordingly, in the some embodiments, the presently disclosed subject matter provides a compound of formula (I):

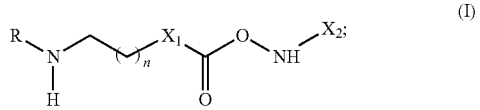

wherein: n is an integer selected from the group consisting of 1, 2, or 3;
$X_1$ is selected from the group consisting of O and $NR_1$;
R and $R_1$ are each independently selected from the group consisting of H, unsubstituted or substituted linear or branched alkyl, and unsubstituted or substituted aryl;
$X_2$ is a leaving group selected from the group consisting of halogen and L-Y, wherein L is a bond, —$SO_2$—, or —O—, and Y is W, alkyl or monocyclic, bicyclic or tricyclic cycloalkyl, heterocycloalkyl, aryl, or heteroaryl, each of which are unsubstituted or substituted with one or more substituent groups selected from W, wherein W is a substituent group selected from the group consisting of substituted or unsubstituted linear or branched alkyl, alkoxyl, perhaloalkyl, hydroxyl, hydroxyalkyl, alkylsulfonyl, alkylsulfanyl, alkylsulfinyl, N-hydroxylsulfonamidyl, carboxyl, carbonyl, carbamoyl, alkylcarbamoyl, halogen, amino, dialkylamino, cycloalkoxyl, cycloalkylsulfanyl, arylsulfanyl, arylsulfinyl, nitro, cyano, nitrile, amide, haloalkyl, substituted or unsubstituted heterocycloalkyl, substituted or unsubstituted aryl, aryloxyl, substituted aryloxyl, cycloalkyl, aralkyloxyl, —$SO_3H$, acyl, —$COR_2$, —$COOR_2$, —$CONR_2R_3$, —$CH(C(O)R_2)_2$, —$SO_2R_2$, or —$COX_3$, wherein $X_3$ is halogen, and $R_2$ and $R_3$ are independently alkyl or aryl, or $R_2$ and $R_3$ are taken together to form a substituted or unsubstituted cycloalkyl or heterocycloalkyl;

and pharmaceutically acceptable salts and hydrates thereof.

Compounds of formula (I) include leaving groups disclosed in U.S. Pat. No. 8,030,356 for "N-hydroxylsulfonamide Derivatives as New Physiologically Useful Nitroxyl Donors," to Toscano et al., issued Oct. 4, 2011, and U.S. Pat. No. 8,277,639, for "N-hydroxylsulfonamide Derivatives as New Physiologically Useful Nitroxyl Donors," to Toscano et al., issued Jul. 24, 2012; U.S. Patent Application Publication Nos. US2011/0136827, for "Bis-Acylated Hydroxylamine Derivatives," to Toscano et al., published Jun. 9, 2011, US2011/0144067, for "N-Acyloxysulfonamide and N-Hydroxy-N-Acylsulfonamide Derivatives," to Toscano et al., published Jun. 16, 2011, US2011/0306614, for "N-Hydroxylsulfonamide Derivatives as New Physiologically Useful Nitroxyl Donors," to Toscano et al., published Dec. 15, 2011, US2012/0258965 for "N-Hydroxylsulfonamide Derivatives as New Physiologically Useful Nitroxyl Donors," to Toscano et al., published Oct. 11, 2012; International PCT Patent Application Publication Nos. WO/2011/071947, for Bis-Acylated Hydroxylamine Derivatives, to Toscano et al., published Jun. 16, 2011, WO/2011/071951, for N-Acyloxysulfonamide and N-Hydoxy-N-Acylfulfonamide Derivatives, to Toscano et al., published Jun. 16, 2011, WO/2009/042970 for N-Hydroxylsulfonamide Derivatives as New Physiologically Useful Nitroxyl Donors, to Toscano et al., published Apr. 2, 2009; International PCT Patent Application No. PCT/US2012/060425 for "N-Substituted Hydroxylamine Derivatives with Carbon-based Leaving Groups," to Toscano et al., filed Oct. 16, 2012; and U.S. Provisional Patent Application No. 61/548,036, for "N-Substituted Hydroxylamine Derivatives with Carbon-Based Leaving Groups as Physiologically Useful Nitroxyl (HNO) Donors," to Toscano et al., filed Oct. 17, 2011, each of which are incorporated herein by reference in their entirety.

In some embodiments, the leaving group comprises a carbon-based leaving group including, but not limited to, those disclosed in International PCT Patent Application No. PCT/US2012/060425 for "N-Substituted Hydroxylamine Derivatives with Carbon-based Leaving Groups," to Toscano et al., filed Oct. 16, 2012; and U.S. Provisional Patent Application No. 61/548,036, for "N-Substituted Hydroxylamine Derivatives with Carbon-Based Leaving Groups as Physiologically Useful Nitroxyl (HNO) Donors," to Toscano et al., filed Oct. 17, 2011, each of which are incorporated herein by reference in their entirety.

Such carbon-based leaving groups can be derived from N-substituted hydroxylamine derivatives provided immediately herein below:

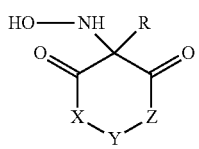

wherein: X and Z are independently selected from —O—, —NR³—, —S—, —CR³—, and —CR³R⁴—; Y is selected from —C(=O)—, —C(=S)—, —C(=NR⁵)—, and —CR⁵R⁶—; R is $C_1$-$C_8$ alkyl, $C_2$-$C_8$ alkenyl, $C_2$-$C_8$ alkynyl, $C_1$-$C_8$ alkoxyl, $C_5$-$C_{10}$ aryl, —C(=O)R⁷, —C(=S)R⁷, —C(=NR⁷)R⁸, and —C(=NOR⁷)R⁸, wherein the alkyl, alkenyl, alkynyl, alkoxyl, and aryl are unsubstituted or substituted with one or more substituents; and R³, R⁴, R⁵, R⁶, R⁷ and R⁸ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents; and

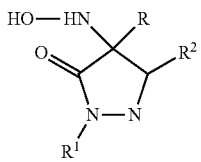

wherein: R is $C_1$-$C_8$ alkyl, $C_2$-$C_8$ alkenyl, $C_2$-$C_8$ alkynyl, $C_1$-$C_8$ alkoxyl, $C_5$-$C_{10}$ aryl, —C(=O)R⁷, —C(=S)R⁷, —C(=NR⁷)R⁸, and —C(=NOR⁷)R⁸, wherein the alkyl, alkenyl, alkynyl, alkoxyl, and aryl are unsubstituted or substituted with one or more substituents; R¹ is selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, and $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents; and R², R⁷ and R⁸ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents.

In particular embodiments, the compound of formula (I) has the following structure:

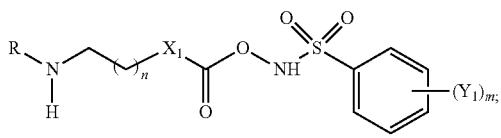

wherein:
m is an integer selected from the group consisting of 0, 1, 2, 3, 4, and 5; and
each $Y_1$ is independently selected from the group consisting of substituted or unsubstituted linear or branched alkyl, alkoxyl, perhaloalkyl, hydroxyl, hydroxyalkyl, alkylsulfonyl, alkylsulfanyl, alkylsulfinyl, N-hydroxylsulfonamidyl, carboxyl, carbonyl, carbamoyl, alkylcarbamoyl, halogen, amino, dialkylamino, cycloalkoxyl, cycloalkylsulfanyl, arylsulfanyl, arylsulfinyl, nitro, cyano, nitrile, amide, haloalkyl, substituted or unsubstituted heterocycloalkyl, substituted or unsubstituted aryl, aryloxyl, substituted aryloxyl, cycloalkyl, aralkyloxyl, —SO₃H, and acyl.

In more particular embodiments, the compound of formula (I) has the following structure:

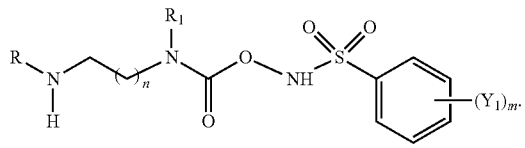

In certain embodiments, R is selected from the group consisting of methyl, isopropyl, benzyl, and phenyl. In other certain embodiments, $R_1$ is selected from the group consisting of methyl, ethyl, sec-butyl, and benzyl.

In other embodiments, the compound of formula (I) has the following structure:

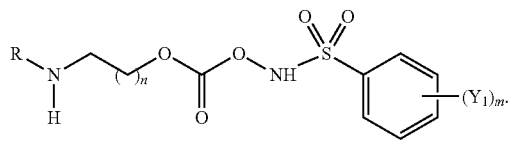

In certain embodiments, R is selected from the group consisting of methyl, isopropyl, t-butyl, benzyl, phenyl, 4-chlorophenyl, and 4-methoxyphenol.

In further embodiments, the presently disclosed subject matter provides a pharmaceutical composition comprising one or more presently disclosed compounds of formula (I) disclosed immediately hereinabove, or a pharmaceutically acceptable salt or hydrate thereof, and a pharmaceutically acceptable carrier.

In yet further embodiments, the presently disclosed subject matter provides a kit comprising one or more presently disclosed compounds of formula (I) disclosed immediately hereinabove, or a pharmaceutically acceptable salt or hydrate thereof, wherein the kit further comprises instructions for use in treating a disease or condition that is responsive to nitroxyl therapy.

For all compounds disclosed herein, where applicable due to the presence of a stereocenter, the compound is intended to embrace all possible stereoisomers of the compound depicted or described. Compositions comprising a compound with at least one stereocenter also are embraced by the presently disclosed subject matter, and include racemic mixtures or mixtures containing an enantiomeric excess of one enantiomer or single diastereomers or diastereomeric mixtures. All such isomeric forms of these compounds are expressly included herein the same as if each and every isomeric form were specifically and individually listed. The compounds herein also may contain linkages (e.g., carbon-carbon bonds) wherein bond rotation is restricted about that particular linkage, e.g., restriction resulting from the presence of a ring or double bond. Accordingly, all cis/trans and E/Z isomers also are expressly included in the presently disclosed subject matter. The compounds herein also may be represented in multiple tautomeric forms, in such instances, the presently disclosed subject matter expressly includes all tautomeric forms of the compounds described herein even though only a single tautomeric form may be represented. Also embraced are compositions of substantially pure compound. A composition of substantially pure compound means that the composition contains no more than 25%, or no more than 15%, or no more than 10%, or no more than 5%, or no more than 3% impurity, or no more than 1% impurity, such as a different biologically active compound, which may include a different stereochemical form of the compound if the composition contains a substantially pure single isomer.

II. METHODS OF TREATMENT

Summary of Heart Failure

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. Often, an individual experiencing heart failure will have some degree of both systolic heart failure and diastolic heart failure.

CHF also is classified according to its severity. The New York Heart Association classifies CHF into four classes: Class I involves no obvious symptoms, with no limitations on physical activity; Class II involves some symptoms during or after normal activity, with mild physical activity limitations; Class III involves symptoms with less than ordinary activity, with moderate to significant physical activity limitations; and Class IV involves significant symptoms at rest, with severe to total physical activity limitations. Typically, an individual progresses through the classes as they live with the condition.

Although CHF is generally thought of as a chronic, progressive condition, it also can develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema and dyspnea.

Common treatment agents for CHF include vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have become standard agents for treating mild to moderate heart failure. Lowes et al, Clin. Cardiol, 23:11111-6 (2000).

Positive inotropic agents include beta-adrenergic agonists, such as dopamine, dobutamine, dopexamine, and isoproterenol. Use of a beta-agonist, however, has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., Fundam. Clin. Pharmacol, 15:95-109 (2001). Accordingly, they have become an established therapy for heart failure. Even subjects that improve under beta-antagonist therapy, however, may subsequently decompensate and require acute treatment with a positive inotropic agent. Unfortunately, as their name suggests, beta-antagonists block the mechanism of action of the positive inotropic beta-agonists that are used in emergency care centers. Bristow et al., J. Card. Fail, 7:8-12 (2001).

Vasodilators, such as nitroglycerin, have been used for a long period of time to treat heart failure. The cause of nitroglycerin's therapeutic effect, however, was not known until late in the last century when it was discovered that the nitric oxide molecule (NO) was responsible for nitroglycerin's beneficial effects. In some subjects experiencing heart failure, a nitric oxide donor is administered in combination with a positive inotropic agent to both cause vasodilation and to increase myocardial contractility. This combined administration, however, can impair the effectiveness of positive inotropic treatment agents. For example, Hart et al, Am. J. Physiol. Heart Circ. Physiol., 281:146-54 (2001) reported that administration of the nitric oxide donor sodium nitroprusside, in combination with the positive inotropic, beta-adrenergic agonist dobutamine, impaired the positive inotropic effect of dobutamine. Hare et al., Circulation, 92:2198-203 (1995) also disclosed the inhibitory effect of nitric oxide on the effectiveness of dobutamine.

As described in U.S. Pat. No. 6,936,639, compounds that donate nitroxyl (HNO) under physiological conditions have both positive inotropic and lusitropic effects and offer significant advantages over existing treatments for failing hearts. Due to their concomitant positive inotropic/lusotropic action and unloading effects, nitroxyl donors were reported as helpful in treating cardiovascular diseases characterized by high resistive load and poor contractile performance. In particular, nitroxyl-donating compounds were reported as useful in the treatment of heart failure, including heart failure in individuals receiving beta-antagonist therapy.

Summary of Ischemia

Ischemia is a condition characterized by an interruption or inadequate supply of blood to tissue, which causes oxygen deprivation in the affected tissue. Myocardial ischemia is a condition caused by a blockage or constriction of one or more of the coronary arteries, such as can occur with atherosclerotic plaque occlusion or rupture. The blockage or constriction causes oxygen deprivation of the non-perfused tissue, which can cause tissue damage. Further, upon reperfusion with subsequent reoxygenation of the tissue, when the blood is able to flow again or the oxygen demand of the tissue subsides, additional injury can be caused by oxidative stress.

Ischemia/reperfusion injury refers to tissue damage caused by oxygen deprivation followed by reoxygenation. The effects of ischemia/reperfusion injury in a subject experiencing the condition can be fatal, particularly when the injury occurs in a critical organ, such as the heart or brain.

Accordingly, compounds and compositions effective in preventing or protecting against ischemia/reperfusion injury would be useful pharmaceuticals. Compounds, such as nitroglycerin, have been used for a long period of time to help control vascular tone and protect against myocardial ischemia/reperfusion injury. It was discovered that the nitric oxide molecule was responsible for nitroglycerin's beneficial effects. This discovery prompted interest in medical uses for nitric oxide and investigations into related species, such as nitroxyl. As reported in U.S. patent application Ser. No. 10/463,084 (U.S. Publication No. 2004/0038947) administration of a compound that donates nitroxyl under physiological conditions, prior to ischemia, can attenuate ischemia/reperfusion injury to tissues, for example, myocardial tissues. This beneficial effect was reported as a surprising result given that nitroxyl was previously reported to increase ischemia/reperfusion injury (See, Ma et al., "Opposite Effects of Nitric Oxide and Nitroxyl on Postischemic Myocardial Injury," Proc. Nat'l Acad. ScL, 96(25):14617-14622 (1999), reporting that administration of Angeli's salt (a nitroxyl donor under physiological conditions) to anesthetized rabbits during ischemia and 5 minutes prior to reperfusion increased myocardial ischemia/reperfusion injury and Takahira et al., "Dexamethasone Attenuates Neutrophil Infiltration in the Rat Kidney in Ischemia/Reperfusion Injury: The Possible Role of Nitroxyl," Free Radical Biology & Medicine, 31(6):809-815 (2001) reporting that administration of Angeli's salt during ischemia and 5 minutes before reperfusion of rat renal tissue contributed to neutrophil infiltration into the tissue, which is believed to mediate ischemia/reperfusion injury). In particular, pre-ischemic administration of Angeli's salt and isopropylamine/NO has been reported to prevent or reduce ischemia/reperfusion injury.

Methods of Using the Compounds and Compositions

The compounds and compositions of formula (I) disclosed herein may be used to treat and/or prevent the onset and/or development of a disease or condition that is responsive to nitroxyl therapy. The presently disclosed subject matter embraces methods of administering to an individual (including an individual identified as in need of such treatment) an effective amount of a compound of formula (I), or a pharmaceutically acceptable salt or hydrate thereof, to produce a desired effect. Identifying a subject in need of such treatment can be in the judgment of a physician, clinical staff, emergency response personnel or other health care professional and can be subjective (e.g., opinion) or objective (e.g., measurable by a test or diagnostic method).

One embodiment provides a method of modulating (including increasing) in vivo nitroxyl levels in an individual in need thereof, the method comprising administering to the individual a compound that donates nitroxyl under physiological conditions or a pharmaceutically acceptable salt or hydrate thereof. An individual is in need of nitroxyl modulation if they have or are suspected of having or are at risk of having or developing a disease or condition that is responsive to nitroxyl therapy.

Particular diseases or conditions embraced by the presently disclosed methods include cardiovascular diseases, such as heart failure or conditions and diseases or conditions that implicate or may implicate ischemia/reperfusion injury. These methods are described in more detail herein below.

Compositions comprising a presently disclosed nitroxyl-donating compound are embraced by the presently disclosed subject matter. The methods described, however, may use more than one nitroxyl-donating compound; for example, the methods may employ Angeli's salt and a presently disclosed compound of Formula (I) or Formula (II) or two or more presently disclosed hydroxylamine derivatives, which may be administered together or sequentially.

Cardiovascular Diseases

Provided herein are methods of treating cardiovascular diseases, such as heart failure, by administering an effective amount of at least one nitroxyl-donating compound to an individual in need thereof. Also provided are methods of administering a therapeutically effective dose of at least one nitroxyl-donating compound in combination with at least one other positive inotropic agent to an individual in need thereof. Further provided are methods of administering a therapeutically effective amount of at least one nitroxyl-donating compound to an individual who is receiving beta-antagonist therapy and who is experiencing heart failure. Methods are provided herein for administering presently disclosed compounds of formula (I) in combination with beta-adrenergic agonists to treat heart failure. Such agonists include dopamine, dobutamine, and isoproterenol, and analogs and derivatives of such compounds. Also provided are methods of administering nitroxyl donors to individuals receiving treatment with beta-antagonizing agents, such as propranolol, metoprolol, bisoprolol, bucindolol, and carvedilol. Further, methods are provided herein for treating specific classifications of heart failure, such as Class HI heart failure and acute heart failure.

Also embraced by the presently disclosed subject matter is a method of treating congestive heart failure (CHF), including acute congestive heart failure, by administering an effective amount at least one nitroxyl-donating compound to an individual in need thereof, which individual may be experiencing heart failure. Also disclosed is a method of treating CHF by administering an effective amount of at least one nitroxyl-donating compound in combination with an effective amount of at least one other positive inotropic agent to an individual in need thereof, which individual may be experiencing heart failure. In one variation, the other positive inotrope is a beta-adrenergic agonist, such as dobutamine. The combined administration of a nitroxyl donor and at least one other positive inotropic agent comprises administering the nitroxyl donor either sequentially with the other positive inotropic agent for example, the treatment with one agent first and then the second agent, or administering both agents at substantially the same time, wherein there is an overlap in performing the administration. With sequential administration, an individual is exposed to the agents at different times, so long as some amount of the first agent, which is sufficient to be therapeutically effective in combination with the second agent, remains in the subject when the other agent is administered. Treatment with both agents at the same time can involve administration of the agents in the same dose, such as a physically mixed dose, or in separate doses administered at the same time.

In a particular embodiment, a nitroxyl donor is administered to an individual experiencing heart failure who is receiving beta-antagonist therapy. A beta-antagonist (also known as a beta-blocker) includes any compound that effectively acts as an antagonist at a subject's beta-adrenergic receptors, and provides desired therapeutic or pharmaceutical results, such as diminished vascular tone and/or heart rate. A subject who is receiving beta-antagonist therapy is any subject to whom a beta-antagonist has been administered, and in whom the beta-antagonist continues to act as an antagonist at the subject's beta-adrenergic receptors. In particular embodiments, a determination of whether a subject is receiving beta-blocking therapy is made by examination of the subject's medical history. In other embodiments, the subject is screened for the presence of beta-blocking agents by chemical tests, such as high-speed liquid chromatography as described in Thevis et al., Biomed Chromatogr., 15:393-402 (2001).

The administration of a nitroxyl-donating compound either alone, in combination with a positive inotropic agent, or to a subject receiving beta-antagonist therapy, is used to treat heart failure of all classifications. In particular embodiments a nitroxyl-donating compound is used to treat early-stage chronic heart failure, such as Class II heart failure. In other embodiments, a nitroxyl-donating compound is used in combination with a positive inotropic agent, such as isoproterenol to treat Class IV heart failure. In still other embodiments a nitroxyl-donating compound is used in combination with another positive inotropic agent, such as isoproterenol to treat acute heart failure. In some embodiments, when a nitroxyl donor is used to treat early stage heart failure, the dose administered is lower than that used to treat acute heart failure. In other embodiments the dose is the same as is used to treat acute heart failure.

Ischemia/Reperfusion Injury

The presently disclosed subject matter embraces methods of treating or preventing or protecting against ischemia/reperfusion injury. In particular, presently disclosed compounds of formula (I) are beneficial for individuals at risk for an ischemic event. Thus, provided herein is a method of preventing or reducing the injury associated with ischemia/reperfusion by administering an effective amount of at least one nitroxyl-donating compound to an individual, preferably prior to the onset of ischemia. A presently disclosed compound of formula (I) may be administered to an individual after ischemia but before reperfusion. A presently disclosed compound of formula (I) also may be administered after ischemia/reperfusion, but where the administration protects against further injury. Also provided is a method in which the individual is demonstrated to be at risk for an ischemic event. Also disclosed is a method of administering a nitroxyl-donating compound to an organ that is to be transplanted in an amount effective to reduce ischemia/reperfusion injury to the tissues of the organ upon reperfusion in the recipient of the transplanted organ.

Nitroxyl donors of the presently disclosed subject matter may thus be used in methods of preventing or reducing injury associated with future ischemia/reperfusion. For example, administration of a nitroxyl donor prior to the onset of ischemia may reduce tissue necrosis (the size of infarct) in at-risk tissues. In live subjects, this may be accomplished by administering an effective amount of a nitroxyl-donating compound to an individual prior to the onset of ischemia. In organs to be transplanted, this is accomplished by contacting the organ with a nitroxyl donor prior to reperfusion of the organ in the transplant recipient. Compositions comprising more than one nitroxyl-donating compound also could be used in the methods described, for example, Angeli's salt and a compound of Formula (I). The nitroxyl-donating compound also can be used in combination with other classes of therapeutic agents that are designed to minimize ischemic injury, such as beta blockers, calcium channel blockers, anti-platelet therapy or other interventions for protecting the myocardium in individuals with coronary artery disease.

One method of administering a nitroxyl donor to live subjects includes administration of the nitroxyl-donating compound prior to the onset of ischemia. This refers only to the onset of each instance of ischemia and would not preclude performance of the method with subjects who have had prior ischemic events, i.e., the method also contemplates administration of nitroxyl-donating compounds to a subject who has had an ischemic event in the past.

Individuals can be selected who are at risk of a first or subsequent ischemic event. Examples include individuals with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia, such as a cerebrovascular accident CVA). In particular examples of the methods, individuals are selected for treatment who are at risk of future ischemia, but who have no present evidence of ischemia (such as electrocardiographic changes associated with ischemia (for example, peaked or inverted T-waves or ST segment elevations or depression in an appropriate clinical context), elevated CKMB, or clinical evidence of ischemia, such as crushing sub-sternal chest pain or arm pain, shortness of breath and/or diaphoresis). The nitroxyl-donating compound also could be administered prior to procedures in which myocardial ischemia may occur, for example an angioplasty or surgery (such as a coronary artery bypass graft surgery). Also embraced is a method of administering a nitroxyl-donating compound to an individual at demonstrated risk for an ischemic event. The selection of an individual with such a status could be performed by a variety of methods, some of which are noted above. For example, an individual with one of more of an abnormal EKG not associated with active ischemia, prior history of myocardial infarction, elevated serum cholesterol, and the like, would be at risk for an ischemic event. Thus, an at-risk individual could be selected by physical testing or eliciting the potential subject's medical history to determine whether the subject has any indications of risk for an ischemic event. If risk is demonstrated based on the indications discussed above, or any other indications that one skilled in the art would appreciate, then the individual would be considered at demonstrated risk for an ischemic event.

Ischemia/reperfusion may damage tissues other than those of the myocardium and the presently disclosed subject matter embraces methods of treating or preventing such damage. In one variation, the method finds use in reducing injury from ischemia/reperfusion in the tissue of the brain, liver, gut, kidney, bowel, or in any other tissue. The methods preferably involve administration of a nitroxyl donor to an individual at risk for such injury. Selecting a person at risk for non-myocardial ischemia could include a determination of the indicators used to assess risk for myocardial ischemia. Other factors, however, may indicate a risk for ischemia/reperfusion in other tissues. For example, surgery patients often experience surgery-related ischemia. Thus, individuals scheduled for surgery could be considered at risk for an ischemic event. The following risk factors for stroke (or a subset of these risk factors) would demonstrate a subject's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, "Preventing ischemic stroke: current approaches to primary and secondary prevention," Postgrad. Med., 107(6):34-50 (2000). Further, complications of untreated infectious diarrhea in the elderly can include myocardial, renal, cerebrovascular and intestinal ischemia. Slotwiner-Nie & Brandt, "Infectious diarrhea in the elderly," Gastroenterol, Clin. N. Am., 30(3): 625-635 (2001). Alternatively, individuals could be selected based on risk factors for ischemic bowel, kidney or liver disease. For example, treatment would be initiated in elderly subjects at risk of hypotensive episodes (such as surgical blood loss). Thus, subjects presenting with such an indication would be considered at risk for an ischemic event. Also embraced is a method of administering a presently disclosed nitroxyl-donating compound to an individual who has any one or more of the conditions listed herein, such as diabetes mellitus or hypertension. Other conditions that may result in ischemia, such as cerebral arteriovenous malformation would be considered to demonstrate risk for an ischemic event.

The method of administering nitroxyl to organs to be transplanted includes administration of nitroxyl prior to removal of the organ from the donor, for example through the perfusion cannulas used in the organ removal process. If the organ donor is a live donor, for example a kidney donor, the nitroxyl donor can be administered to the organ donor as described above for a subject at risk for an ischemic event. In other cases the nitroxyl donor can be administered by storing the organ in a solution comprising the nitroxyl donor. For example, the nitroxyl donor can be included in the organ preservation solution, such as University of Wisconsin "UW" solution, which is a solution comprising hydroxyethyl starch substantially free of ethylene glycol, ethylene chlorohydrin, and acetone (see U.S. Pat. No. 4,798,824).

Accordingly, in some embodiments, the presently disclosed subject matter provides a method for modulating an in vivo nitroxyl level in a subject in need thereof, the method comprising administering to the subject one or more presently disclosed compounds of formula (I) disclosed herein, or a pharmaceutically acceptable salt or hydrate thereof, in an amount effective to modulate the in vivo nitroxyl level.

In other embodiments, the presently disclosed subject matter provides a method for treating, preventing, or delaying the onset or development of a disease or condition that is responsive to nitroxyl therapy, the method comprising administering to a subject in need thereof a therapeutically effective amount of one or more presently disclosed compounds of formula (I) disclosed herein, or a pharmaceutically acceptable salt or hydrate thereof.

In certain embodiments, the presently disclosed method of treatment further comprises administering to the subject in combination with one or more presently disclosed compounds of formula (I) disclosed herein, a second therapeutic agent selected from the group consisting of an angiotensin I-converting enzyme (ACE) inhibitor, an alpha-adrenergic blocker, a central adrenergic inhibitor, a beta-adrenergic blocker, an angiotensin II receptor blocker, a calcium channel blocker, a vasodilator, a phosphodiesterase (PDE) inhibitor, an HMG-CoA reductase inhibitor, a cholesterol-lowering agent, an antiarrhythmic agent, a digitalis drug, a nitrate, a diuretic, an anticoagulant, an antiplatelet agent, a thrombolytic agent, an antioxidant, and combinations thereof. In certain embodiments, the antioxidant comprises edaravone, a potent antioxidant currently in clinical use for treating stroke and cardiovascular disease. See, e.g., Higashi, Y., et al., "Edaravone (3-Methyl-1-Phenyl-2-Pyrazoin-5-one), A Novel Free Radical Scavenger, for Treatment of Cardiovascular Diseases," Recent Patents on Cardiovascular Drug Discovery, 1, 85-93 (2006); Watanabe, T., "The Novel Antioxidant Edaravone: From Bench to Bedside," Cardiovascular Therapeutics, 26, 101-114 (2008). Further, Angeli's salt, a classic HNO donor, has been reported to produce a small amount of hydroxyl radical under certain conditions. See, e.g., Hughes, M. N., and Wimbledon, P. E., "The Chemistry of Trioxodinitrates. Part I. Decomposition of Sodium Trioxodinitrate (Angeli's Salt) in Aqueous Solution," J. Chem. Soc. Dalton, 703-707 (1976); Ivanova, J., et al., "Formation of Nitroxyl and Hydroxyl Radical in Solutions of Sodium Trioxodinitrate," J. Biol. Chem. 278(44): 42701-42708 (2003).

In particular embodiments, the disease or condition treated by the presently disclosed methods is selected from the group consisting of a cardiovascular disease, congestive heart failure, and myocardial ischemia/reperfusion injury.

Pharmaceutical Composition, Dosage Forms and Treatment Regimens

Also included are pharmaceutically acceptable compositions comprising a presently disclosed compound or a pharmaceutically acceptable salt or hydrate thereof and any of the methods may employ the presently disclosed compounds of formula (I) as a pharmaceutically acceptable composition. Generally, the presently disclosed compounds of formula (I) exhibit very good water solubility. This characteristic can be an advantage over many Piloty's acid derivatives and many acyloxy nitroso compounds, which can have poor water solubility.

A pharmaceutically acceptable composition includes one or more of the presently disclosed compounds of formula (I) together with a pharmaceutically acceptable carrier. The pharmaceutical compositions of the presently disclosed subject matter include those suitable for oral, rectal, nasal, topical (including buccal and sublingual), vaginal or parenteral (including subcutaneous, intramuscular, intravenous and intradermal) administration.

In particular embodiments, the presently disclosed subject matter provides a pharmaceutical composition comprising one or more presently disclosed compounds of formula (I) in combination with Captisol® (CyDex Pharmaceuticals, Inc., Lenexa, Kans., United States of America), which is based on a modified cyclodextrin molecule that can improve the solubility and bioavailability of the presently disclosed pharmaceutically active compounds. More particularly, Captisol® is one of a series of anionically charged sulfobutyl ether beta-cyclodextrins (SBE-CDs). One of ordinary skill in the art would recognize that other SBE-CDs also could be suitable for use with the presently disclosed compounds.

The compounds or compositions may be prepared as any available dosage form. Unit dosage forms also are intended, which include discrete units of the compound or composition, such as capsules, sachets or tablets each containing a predetermined amount of the compound; as a powder or granules; as a solution or a suspension in an aqueous liquid or a nonaqueous liquid; or as an oil-in-water liquid emulsion or a water-in-oil liquid emulsion, or packed in liposomes and as a bolus, and the like.

A tablet containing the compound or composition may be made by compression or molding, optionally with one or more accessory ingredients. Compressed tablets may be prepared by compressing in a suitable machine the active ingredient in a free-flowing form, such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued U.S. Patents, some of which include, but are not limited to, U.S. Pat. Nos. 4,369,174 and 4,842,866, and references cited therein. Coatings can be used for delivery of compounds to the intestine (see, e.g., U.S. Pat. Nos. 6,638,534, 5,217,720 and 6,569,457, and references cited therein). A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis, such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions, which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use.

Extemporaneous injection solutions and suspensions may be prepared from sterile powders, granules and tablets.

Administration of the compounds or compositions to an individual may involve systemic exposure or may be local administration, such as when a compound or composition is to be administered at the site of interest. Various techniques can be used for providing the subject compositions at the site of interest, such as via injection, use of catheters, trocars, projectiles, pluronic gel, stems, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. The methods of the presently disclosed subject matter embrace administration of the compounds to an organ to be donated (such as to prevent ischemia/reperfusion injury). Accordingly, organs that are removed from one individual for transplant into another individual may be bathed in a medium containing or otherwise exposed to a compound or composition as described herein.

The presently disclosed compounds of formula (I) may be administered in any suitable dosage amount, which may include dosage levels of about 0.0001 to 4.0 grams once per day (or multiple doses per day in divided doses) for adults. Thus, in certain embodiments of the presently disclosed subject matter, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.1 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). The dosing interval can be adjusted according to the needs of the individual. For longer intervals of administration, extended release or depot formulations can be used. The dosing can be commensurate with intravenous administration. For instance, the compound can be administered, such as in a pharmaceutical composition that is amenable to intravenous administration, in an amount of between about 0.01 µg/kg/min to about 100 µg/kg/min or between about 0.05 µg/kg/min to about 95 µg/kg/min or between about 0.1 µg/kg/min to about 90 µg/kg/min or between about 1.0 µg/kg/min to about 80 µg/kg/min or between about 10.0 µg/kg/min to about 70 µg/kg/min or between about 20 µg/kg/min to about 60 µg/kg/min or between about 30 µg/kg/min to about 50 µg/kg/min or between about 0.01 µg/kg/min to about 1.0 µg/kg/min or between about 0.01 µg/kg/min to about 10 µg/kg/min or between about 0.1 µg/kg/min to about 1.0 µg/kg/min or between about 0.1 µg/kg/min to about 10 µg/kg/min or between about 1.0 µg/kg/min to about 5 µg/kg/min or between about 70 µg/kg/min to about 100 µg/kg/min or between about 80 µg/kg/min to about 90 µg/kg/min. In one variation, the compound is administered to an individual, such as in a pharmaceutical composition that is amenable to intravenous administration, in an amount of at least about 0.01 µg/kg/min or at least about 0.05 µg/kg/min or at least about 0.1 µg/kg/min or at least about 0.15 µg/kg/min or at least about 0.25 µg/kg/min or at least about 0.5 µg/kg/min or at least about 1.0 µg/kg/min or at least about 1.5 µg/kg/min or at least about 5.0 µg/kg/min or at least about 10.0 µg/kg/min or at least about 20.0 µg/kg/min or at least about 30.0 µg/kg/min or at least about 40.0 µg/kg/min or at least about 50.0 µg/kg/min or at least about 60.0 µg/kg/min or at least about 70.0 µg/kg/min or at least about 80.0 µg/kg/min or at least about 90.0 µg/kg/min or at least about 100.0 µg/kg/min or more. In another variation, the compound is administered to an individual, such as in a pharmaceutical composition that is amenable to intravenous administration, in an amount of less than about 100.0 µg/kg/min or less than about 90.0 µg/kg/min or less than about 80.0 µg/kg/min or less than about 80.0 µg/kg/min or less than about 70.0 µg/kg/min or less than about 60.0 µg/kg/min or less than about 50.0 µg/kg/min or less than about 40.0 µg/kg/min or less than about 30.0 µg/kg/min or less than about 20.0 µg/kg/min or less than about 10.0 µg/kg/min or less than about 5.0 µg/kg/min or less than about 2.5 µg/kg/min or less than about 1.0 µg/kg/min or less than about 0.5 µg/kg/min or less than about 0.05 µg/kg/min or less than about 0.15 µg/kg/min or less than about 0.1 µg/kg/min or less than about 0.05 µg/kg/min or less than about 0.01 µg/kg/min.

The presently disclosed subject matter further provides kits comprising one or more compounds as described herein.

The kits may employ any of the compounds disclosed herein and instructions for use. The compound may be formulated in any acceptable form. The kits may be used for any one or more of the uses described herein, and, accordingly, may contain instructions for any one or more of the stated uses (e.g., treating and/or preventing and/or delaying the onset and/or the development of heart failure or ischemia/reperfusion injury).

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions also are acceptable, relating to the use of component(s) of the methods of the presently disclosed subject matter (e.g., treating, preventing and/or delaying the onset and/or the development of heart disease or ischemia/reperfusion injury). The instructions included with the kit generally include information as to the components and their administration to an individual.

III. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

"Aralkyl" refers to a residue in which an aryl moiety is attached to the parent structure via an alkyl residue. Examples include benzyl (—CH$_2$-Ph), phenethyl (—CH$_2$CH$_2$Ph), phenylvinyl (—CH=CH-Ph), phenylallyl and the like.

"Acyl" refers to and includes the groups —C(O)H, —C(O)alkyl, —C(O)substituted alkyl, —C(O)alkenyl, —C(O)substituted alkenyl, —C(O)alkynyl, —C(O)substituted alkynyl, —C(O)cycloalkyl, —C(O)substituted cycloalkyl, —C(O)aryl, —C(O)substituted aryl, —C(O)heteroaryl, —C(O)substituted heteroaryl, —C(O)heterocyclic, and —C(O)substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein or otherwise known in the art.

"Heterocyclyl" or "Heterocycloalkyl" refers to a cycloalkyl residue in which one to four of the carbons is replaced by a heteroatom, such as oxygen, nitrogen or sulfur. Examples of heterocycles whose radicals are heterocyclyl groups include tetrahydropyran, morpholine, pyrrolidine, piperidine, thiazolidine, oxazole, oxazoline, isoxazole, dioxane, tetrahydrofuran and the like. A specific example of a heterocyclyl residue is tetrahydropyran-2-yl.

"Substituted heterocyclo" or "substituted heterocylcoalkyl" refers to an heterocyclyl group having from 1 to 5 substituents. For instance, a heterocyclyl group substituted with 1 to 5 groups, such as halo, nitro, cyano, oxo, aryl, alkoxyl, alkyl, acyl, acylamino, amino, hydroxyl, carboxyl, carboxylalkyl, thiol, thioalkyl, heterocyclyl, —OS(O)$_2$-alkyl, and the like is a substituted alkyl. A particular example of a substituted heterocylcoalkyl is N-methylpiperazino.

"Alkyl" intends linear hydrocarbon structures having 1 to 20 carbon atoms, preferably 1 to 12 carbon atoms and more preferably 1 to 8 carbon atoms. Alkyl groups of fewer carbon atoms are embraced, such as so-called "lower alkyl" groups having 1 to 4 carbon atoms. "Alkyl" also intends branched or cyclic hydrocarbon structures having 3 to 20 carbon atoms, preferably 3 to 12 carbon atoms and more preferably 3 to 8 carbon atoms. For any use of the term "alkyl," unless clearly indicated otherwise, it is intended to embrace all variations of alkyl groups disclosed herein, as measured by the number of carbon atoms, the same as if each and every alkyl group was explicitly and individually listed for each usage of the term. For instance, when a group, such as R may be an "alkyl," intended is a $C_1$-$C_{20}$ alkyl or a $C_1$-$C_{12}$ alkyl or a $C_1$-$C_8$ alkyl or a lower alkyl or a $C_2$-$C_{20}$ alkyl or a $C_3$-$C_{12}$ alkyl or a $C_3$-$C_8$ alkyl. The same is true for other groups listed herein, which may include groups under other definitions, where a certain number of atoms is listed in the definition. When the alkyl group is cyclic, it also may be referred to as a cycloalkyl group and have e.g., 3 to 20 annular carbon atoms, preferably 3 to 12 annular carbon atoms and more preferably 3 to 8 annular carbon atoms. When an alkyl residue having a specific number of carbons is named, all geometric isomers having that number of carbons are intended to be encompassed; thus, for example, "butyl" is meant to include n-butyl, sec-butyl, iso-butyl and t-butyl; "propyl" includes n-propyl and iso-propyl. Examples of alkyl groups include methyl, ethyl, n-propyl, i-propyl, t-butyl, n-heptyl, octyl, cyclopentyl, cyclopropyl, cyclobutyl, norbornyl, and the like. One or more degrees of unsaturation may occur in an alkyl group. Thus, an alkyl group also embraces alkenyl and alkynyl residues. "Alkenyl" is understood to refer to a group of 2 or more carbon atoms, such as 2 to 10 carbon atoms and, more preferably 2 to 6 carbon atoms and having at least 1 and preferably from 1-2 sites of alkenyl unsaturation. Examples of an alkenyl group include —C=CH$_2$, —CH$_2$CH=CHCH$_3$ and —CH$_2$CH=CH—CH=CH$_2$. "Alkynyl" refers to alkynyl group preferably having from 2 to 10 carbon atoms and more preferably 3 to 6 carbon atoms and having at least 1 and preferably from 1-2 sites of alkynyl unsaturation, such as the moiety —C≡CH. Alkyl also is used herein to denote an alkyl residue as part of a larger functional group and when so used, is taken together with other atoms to form another functional group. For instance, reference to —C(O)Oalkyl intends an ester functional group, where the alkyl portion of the moiety may be any alkyl group, and provide by way of example only, the functional group —C(O)OCH$_3$, —C(O)(O)CH=CH$_2$ and the like. Another example of an alkyl group as part of a larger structure includes the residue —NHC(O)alkylC(O)OH, which e.g., may be NHC(O)CH$_2$CH$_2$C(O)OH when alkyl is —CH$_2$CH$_2$—.

"Substituted alkyl" refers to an alkyl group having from 1 to 5 substituents. For instance, an alkyl group substituted with a group, such as halo, nitro, cyano, oxo, aryl, alkoxyl, acyl, acylamino, amino, hydroxyl, carboxyl, carboxylalkyl, thiol, thioalkyl, heterocyclyl, —OS(O)$_2$-alkyl, and the like is a substituted alkyl. Likewise, "substituted alkenyl" and "substituted alkynyl" refer to alkenyl or alkynyl groups having 1 to 5 substituents.

As used herein the term "substituent" or "substituted" means that a hydrogen radical on a compound or group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxyl, mercaptoalkoxyl, aryl, heteroaryl, cyclyl, heterocyclyl, wherein alkyl, alkenyl, alkyloxyl, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=Nalkyl). In other embodiments, substituents on any group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) can be at any atom of that group (such as on a carbon atom of the primary carbon chain of a substituted alkyl group or on a substituent already present on a substituted alkyl group) or at any atom of, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxyl, aryloxyl, hydroxyl, hydroxylalkyl, oxo (i.e., carbonyl), carboxyl, formyl, alkylcarbonyl, alkylcarbonylalkyl, alkoxycarbonyl, alkylcarbonyloxyl, aryloxycarbonyl, heteroaryloxyl, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy. Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, NO$_2$, OR$^{11}$, SR$^{11}$, S(O)$_2$OR$^{11}$, NR$^{11}$R$^{12}$, C$_1$-C$_2$ perfluoroalkyl, C$_1$-C$_2$ perfluoroalkoxyl, 1,2-methylenedioxy, (=O), (=S), (=NR$^{11}$), C(O)OR$^{11}$, C(O)R$^{11}$R$^{12}$, OC(O)NR$^{11}$R$^{12}$, NR$^{11}$C(O)NR$^{11}$R$^{12}$, C(NR$^{12}$)NR$^{11}$R$^{12}$, NR$^{11}$C(NR$^{10}$NR$^{11}$R$^{12}$, S(O)$_2$NR$^{11}$R$^{12}$R$^{13}$, C(O)H, C(O)R$^{13}$, NR$^{11}$C(O)R$^{13}$, Si(R$^{11}$)$_3$, OSi(R$^{11}$)$_3$, Si(OH)$_2$R$^{11}$, B(OH)$_2$, P(O)(OR$^{11}$)$_2$, S(O)R$^{13}$, or S(O)$_2$R$^{13}$. Each R$^{11}$ is independently hydrogen, C$_1$-C$_6$ alkyl optionally substituted with cycloalkyl, aryl, heterocyclyl, or heteroaryl. Each R$^{12}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and Ci-C$_4$ alkyl in each R$^{11}$, R$^{12}$ and R$^{13}$ can optionally be substituted with halogen, CN, C$_1$-C$_4$ alkyl, OH, Ci-C$_4$ alkoxyl, COOH, C(O)OCi-C$_4$ alkyl, NH$_2$, C$_1$-C$_4$ alkylamino, or C$_1$-C$_4$ dialkylamino. Substituents also can be "electron-withdrawing groups."

"Electron withdrawing group" refers to groups that reduce electron density of the moiety to which they are attached (relative to the density of the moiety without the substituent). Such groups include, for example, F, Cl, Br, I, —CN, —CF$_3$, —NO$_2$, —SH, —C(O)H, —C(O)alkyl, —C(O)Oalkyl, —C(O)OH, —C(O)Cl, —S(O)$_2$OH, —S(O)$_2$NHOH, —NH$_3$ and the like.

"Halo" refers to fluorine, chlorine, bromine or iodine.

"Alkylsulfonyl" refers to groups —SO$_2$alkyl and —SO$_2$substituted alkyl, which includes the residues —SO$_2$cycloalkyl, —SO$_2$substituted cycloalkyl, —SO$_2$alkenyl, —SO$_2$Substituted alkenyl, —SO$_2$alkynyl, —SO$_2$substituted alkynyl, where alkyl, substituted alkyl, alkenyl, substituted alkenyl, alkynyl, substituted alkynyl, cycloalkyl and substituted cycloalkyl are as defined herein.

'W-hydroxylsulfonamidyl" refers to —S(O)$_2$NROH, where R is H or alkyl.

"Perhaloalkyl" refers to an alkyl group where each H of the hydrocarbon is replaced with F. Examples of perhalo groups include —CF$_3$ and —CF$_2$CF$_3$.

"Aryl" intends a monocyclic, bicyclic or tricyclic aromatic ring. An aryl group is preferably a 5- or 6-membered aromatic or heteroaromatic ring containing 0-3 annular heteroatoms selected from O, N, or S; a bicyclic 9- or 10-membered aromatic or heteroaromatic ring system (meaning the ring system has 9 or 10 annular atoms) containing 0-3 annular heteroatoms selected from O, N, or S; or a tricyclic 13- or 14-membered aromatic or heteroaromatic ring system (meaning the ring system has 13 or 14 annular atoms) containing 0-3 annular heteroatoms selected from O, N, or S. Examples of groups whose radicals are aryl groups include e.g., benzene, naphthalene, indane, tetralin, imidazole, pyridine, indole, thiophene, benzopyranone, thiazole, furan, benzimidazole, benzoxazole, benzthiazole, quinoline, isoquinoline, quinoxaline, pyrimidine, pyrazine, tetrazole and pyrazole.

"Substituted aryl" refers to a group having from 1 to 3 substituents. For instance, an aryl group substituted with 1 to 3 groups, such as halo, nitro, cyano, oxo, aryl, alkoxyl, alkyl, acyl, acylamino, amino, hydroxyl, carboxyl, carboxylalkyl, thiol, thioalkyl, heterocyclyl, —OS(O)$_2$-alkyl, and the like is a substituted aryl.

"Alkoxy" refers to an alkyl group that is connected to the parent structure through an oxygen atom (—O-alkyl). When a cycloalkyl group is connected to the parent structure through an oxygen atom, the group also may be referred to as a cycloalkoxyl group. Examples include methoxyl, ethoxyl, propoxyl, isopropoxyl, cyclopropyloxyl, cyclohexyloxyl and the like. A "perhaloalkoxyl" intends a perhaloalkyl group attached to the parent structure through an oxygen, such as the residue —O—CF$_3$.

"Aryloxy" refers to an aryl group that is connected to the parent structure through an oxygen atom (—O-aryl), which by way of example includes the residues phenoxyl, naphthoxyl, and the like. "Substituted aryloxyl" refers to a substituted aryl group connected to the parent structure through an oxygen atom (—O-substituted aryl).

"Alkylsulfanyl" refers to an alkyl group that is connected to the parent structure through a sulfur atom (—S-alkyl) and refers to groups —S-alkyl and —S— substituted alkyl, which includes the residues —S-cycloalkyl, —S-substituted cycloalkyl, —S-alkenyl, —S-substituted alkenyl, —S-alkynyl, —S-substituted alkynyl, where alkyl, substituted alkyl, alkenyl, substituted alkenyl, alkynyl, substituted alkynyl, cycloalkyl and substituted cycloalkyl are as defined herein. When a cycloalkyl group is connected to the parent structure through an sulfur atom, the group also may be referred to as a cycloalkylsulfanyl group. By way of example, alkylsulfanyl includes —S—CH(CH$_3$), —S—CH$_2$CH$_3$ and the like.

"Alkylsulfinyl" refers to an alkyl group that is connected to the parent structure through a S(O) moiety and refers to groups —S(O)alkyl and —S(O)substituted alkyl, which includes the residues —S(O)cycloalkyl, —S(O)substituted cycloalkyl, —S(O)alkenyl, —S(O)substituted alkenyl, —S(O)alkynyl, —S(O)substituted alkynyl, where alkyl, substituted alkyl, alkenyl, substituted alkenyl, alkynyl, substituted alkynyl, cycloalkyl and substituted cycloalkyl are as defined herein. By way of example, alkylsulfinyl includes the residues —S(O)CH(CH$_3$), —S(O)CH$_3$, —S(O)cyclopentane and the like.

"Arylsulfinyl" refers to an aryl group that is connected to the parent structure through a S(O) moiety, which by way of example includes the residue —S(O)Ph.

"Dialkylamino" refers to the group —NR$_2$ where each R is an alkyl group. Examples of dialkylamino groups include —N(CH$_3$)$_2$, —N(CH$_2$CH$_2$CH$_2$CH$_3$)$_2$, and N(CH$_3$)(CH$_2$CH$_2$CH$_2$CH$_3$).

"Carboxyl" refers to —C(O)OH.

"Carboxyl ester" as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Acylamino" refers to the group —C(O)NR$_3$R$_b$ where each R$_a$ and R$_b$ group is independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring. An examples of an acylamino moiety includes —C(O)morpholino.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$R-heterocyclic, and —SO$_2$NR-substituted heterocyclic where R is hydrogen or alkyl, or —SO$_2$NR$_2$, where the two R groups are taken together and with the nitrogen atom to which they are attached to form a heterocyclic or substituted heterocyclic ring.

"Carbonylamino" refers to the groups —CONH$_2$, —CONR-alkyl, —CONR-substituted alkyl, —CONR-alkenyl, —CONR-substituted alkenyl, —CONR-alkynyl, —CONR-substituted alkynyl, —CONR-aryl, —CONR-substituted aryl, —CONR-heteroaryl, —CONR-substituted heteroaryl, —CONR-heterocyclic, and —CONR-substituted heterocyclic where R is hydrogen or alkyl, or —CONR$_2$, where the two R groups are taken together and with the nitrogen atom to which they are attached to form a heterocyclic or substituted heterocyclic ring.

"Pharmaceutically acceptable salt" refers to pharmaceutically acceptable salts of a compound described herein, such as a hydroxylamine derivative, or other presently disclosed nitroxyl donor, which salts may be derived from a variety of organic and inorganic counter ions well known in the art and include, by way of example only, sodium, potassium, calcium, magnesium, ammonium, tetraalkylammonium, and the like; when the molecule contains a basic functionality, salts of organic or inorganic acids, such as hydrochloride, hydrobromide, tartrate, mesylate, acetate, maleate, oxalate and the like. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt may be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals, such as sodium, potassium, and lithium; hydroxides of alkaline earth metal, such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl) amine, or tri-(2-hydroxyethyl)amine; N-methyl-D-glucamine; and amino acids, such as arginine, lysine, and the like. A salt also may be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

Unless clearly indicated otherwise, "an individual" as used herein intends a mammal, including but not limited to a human. An "individual" can be a "subject," as those terms are used interchangeably herein. Accordingly, the "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

The term "effective amount" intends such amount of a compound or a pharmaceutically acceptable salt thereof, which in combination with its parameters of efficacy and toxicity, as well as based on the knowledge of the practicing specialist should be effective in a given therapeutic form. As is understood in the art, an effective amount may be in one or more doses.

As used herein, "treatment" or "treating" is an approach for obtaining a beneficial or desired result, including clinical results. For purposes of the presently disclosed subject matter, beneficial or desired results include but are not limited to inhibiting and/or suppressing the onset and/or development of a disease or condition that is responsive to nitroxyl therapy or reducing the severity of such disease or condition, such as reducing the number and/or severity of symptoms associated with the disease or condition, increasing the quality of life of those suffering from the disease or condition, decreasing the dose of other medications required to treat the disease or condition, enhancing the effect of another medication an individual is taking for the disease or condition and prolonging survival of individuals having the disease or condition. The disease or condition may be a cardiovascular disease or condition, which includes, but is not limited to, coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure, such as acute congestive heart failure and acute decompensated heart failure. Related symptoms that may be alleviated by the methods herein include shortness of breath, fatigue, swollen ankles or legs, angina, loss of appetite, weight gain or loss, associated with aforementioned diseases or disorders. The disease or condition may involve ischemia/reperfusion injury.

As used herein, "preventing" refers to reducing the probability of developing a disorder or condition in an individual who does not have, but is at risk of developing a disorder or condition."

An individual "at risk" may or may not have a detectable disease or condition, and may or may not have displayed a detectable disease or condition prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Nitroxyl" refers to the species HNO.

As used herein, a compound is a "nitroxyl donor" if it donates nitroxyl under physiological conditions. As used herein, the presently disclosed nitroxyl donors alternatively may be referred to as "a compound" or "the compound." Preferably, the nitroxyl donor is capable of donating an effective amount of nitroxyl in vivo and has a safety profile indicating the compound would be tolerated by an individual in the amount necessary to achieve a therapeutic effect. One of ordinary skill in the art would be able to determine the safety of administering particular compounds and dosages to live subjects. One of skill in the art also may determine whether a compound is a nitroxyl donor by evaluating whether it releases HNO under physiological conditions. Compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in water, in a sealed container. After sufficient time for disassociation has elapsed, such as from several minutes to several hours, the headspace gas is withdrawn and analyzed to determine its composition, such as by gas chromatography and/or mass spectroscopy. If the gas $N_2O$ is formed (which occurs by HNO dimerization), the test is positive for nitroxyl donation and the compound is a nitroxyl donor. The level of nitroxyl-donating ability may be expressed as a percentage of a compound's theoretical maximum. A compound that donates a "significant level of nitroxyl" intends a compound that donates 40% or more or 50% or more of its theoretical maximum amount of nitroxyl. In one variation, the compounds for use herein donate 60% or more of the theoretical maximum amount of nitroxyl. In another variation, the compounds for use herein donate 70% or more of the theoretical maximum amount of nitroxyl. In another variation, the compounds for use herein donate 80% or more of the theoretical maximum amount of nitroxyl. In another variation, the compounds for use herein donate 90% or more of the theoretical maximum amount of nitroxyl. In yet another variation, the compounds for use herein donate between about 70% and about 90% of the theoretical maximum amount of nitroxyl. In yet another variation, the compounds for use herein donate between about 85% and about 95% of the theoretical maximum amount of nitroxyl. In yet another variation, the compounds for use herein donate between about 90% and about 95% of the theoretical maximum amount of nitroxyl.

Compounds that donate less than 40% or less than 50% of their theoretical amount of nitroxyl are still nitroxyl donors and may be used in the presently disclosed subject matter. A compound that donates less than 50% of the theoretical amount of nitroxyl may be used in the methods described, and may require higher dosing levels as compared to compounds that donate a significant level of nitroxyl. Nitroxyl donation also can be detected by exposing the test compound to metmyoglobin ($Mb^{3+}$). Nitroxyl reacts with $Mb^{3+}$ to form an $Mb^{2+}$-NO complex, which can be detected by changes in the ultraviolet/visible spectrum or by Electron Paramagnetic Resonance (EPR). The $Mb^{2+}$-NO complex has an EPR signal centered around a g-value of about 2. Nitric oxide, on the other hand, reacts with $Mb^{3+}$ to form an $Mb^{3+}$-NO complex that is EPR silent. Accordingly, if the candidate compound reacts with $Mb^{3+}$ to form a complex detectable by common methods, such as ultraviolet/visible or EPR, then the test is positive for nitroxyl donation. Testing for nitroxyl donation may be performed at physiologically relevant pH.

A "positive inotrope" as used herein is an agent that causes an increase in myocardial contractile function. Such an agent includes a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds also are intended. For example, U.S. Pat. No. 4,663,351 describes a dobutamine prodrug that can be administered orally. One of ordinary skill in the art would be able to determine if a compound is capable of causing positive inotropic effects and also additional beta-agonist compounds. In particular embodiments, the beta-receptor agonist is selective for the beta-1 receptor. In other embodiments, however, the beta-agonist is selective for the beta-2 receptor, or is not selective for any particular receptor.

Diseases or conditions that are "responsive to nitroxyl therapy" intends any disease or condition in which administration of a compound that donates an effective amount of nitroxyl under physiological conditions treats and/or prevents the disease or condition, as those terms are defined herein. A disease or condition whose symptoms are suppressed or diminished upon administration of nitroxyl donor is a disease or condition responsive to nitroxyl therapy. Non-limiting examples of diseases or conditions that are responsive to nitroxyl therapy include coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure, such as acute congestive heart failure and acute decompensated heart failure. Other cardiovascular diseases or conditions also are intended, as are diseases or conditions that implicate ischemia/reperfusion injury.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthetic Procedures

General Synthesis of N-Acylamino Ethanols

Method A: 2-(4-methoxy-phenylamino)-ethanol

To a solution of 1 equivalent of 4-methoxyaniline (5 g) in 200 mL ethyl acetate, 1 equivalent HBr (33% solution in acetic acid) is added. The resultant precipitate is filtered. A neat mixture of the precipitate and ethylene carbonate is heated at 130° C. until a crude $^1$H NMR of the reaction mixture indicates the consumption of the ethylene carbonate. The reaction is cooled and washed with 10% NaOH solution. The solution is extracted twice with ethyl acetate. The organic phases are combined, dried over MgSO$_4$, and the solvent is evaporated.

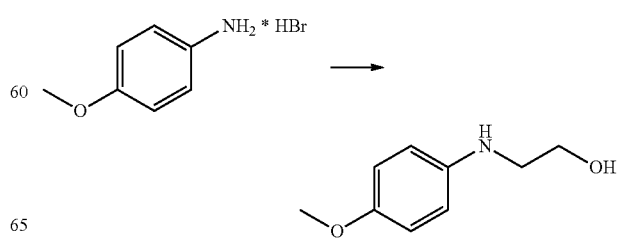

Method B: 2-(4-chloro-phenylamino)-ethanol

To a solution of 1 mL ethylene glycol in 50 mL dichloromethane 1.2 equivalents of $SOCl_2$ is slowly added. After addition, the solution is refluxed until crude $^1H$ NMR of the reaction mixture indicates complete consumption of ethylene glycol and the appearance of ethylene sulfide. Upon completion, the solvent is evaporated and 1 equivalent of 4-chloroaniline is added. The neat mixture is heated at 130° C. until $^1H$ NMR indication of complete reaction.

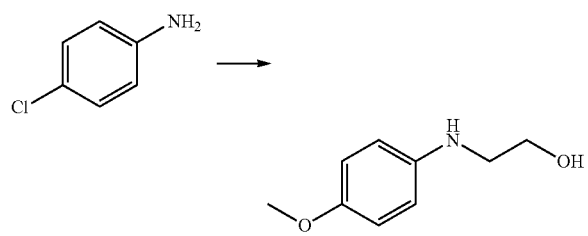

General Synthesis of N-(tert-Butoxycarbonyl)-N-Alkylamino Alcohols

Method A: Alkylamino alcohols and 4-methoxy-phenyl amino alcohols

To di-tert-butyl-dicarbonate (10 g) at room temperature 1 equivalent of amino alcohol is added. When bubbling due to gas evolution ceased, the residue is quenched with water. The aqueous layer is extracted with ether or ethyl acetate. The organic layer is dried over $MgSO_4$ and the solvent is evaporated. Yields were typically quantitative.

Method B: 2-(tert-butylamino)-ethanols and 4-chloro-phenylamino alcohols

The amino alcohol (5 g) is added to 1 equivalent of di-tert-butyl-dicarbonate as in method A. The resultant mixture dissolved in and refluxed in 50 mL chloroform. After completion of the reaction, as determined by $^1H$ NMR, the workup followed that of Method A. Yields were typically quantitative.

Method C: 2-Phenylamino ethanol

To di-tert-butyl-dicarbonate (10 g), 1 equivalent of 2-phenylamino ethanol is added. To this mixture 0.10 equivalent of $I_2$ is added. The solution is stirred for two hours. A solution of 10% $Na_2S_2O_3$ is added. The crude amino ethanol is extracted with dichloromethane, dried, and evaporated. The crude residue was crystallized with petroleum ether. Yields were typically 75-100%.

General Synthesis of 2-(N-tert-Butoxycarbonyl)-2-N-Alkylamino-Acetaldehydes

The synthesis employed a slightly modified literature procedure. Kato, S., et al., *J. Chem. Soc., Perkin Trans.* 1 1997, 3219-3226. To a solution of 2-(N-tert-butoxycarbonyl)-N-alkylamino-ethanol (2 g) in 50 mL dichloromethane, 10 equivalents of dimethylsulfoxide and 2 equivalents of triethylamine were added. The mixture was cooled to 15° C. In portions, 2 equivalents of sulfur trioxide-pyridine complex was added to the solution. Care was taken to keep the temperature below 20° C. during the addition. The reaction was allowed to stir for 2 hours. The reaction mixture was quenched by the addition of water. The organic layer was extracted, dried with $MgSO_4$, and the solvent was evaporated yielding the desired product. Yields were typically 90-100%.

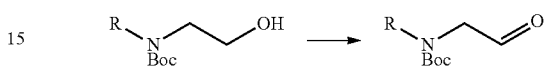

General Synthesis of N-(tert-Butoxycarbonyl)-N-Alkyl-N'-Alkyl-Ethylenediamine The synthesis employed a slightly modified literature procedure. Kato, S., et al., *J. Chem. Soc., Perkin Trans.* 1 1997, 3219-3226. To a solution of 2-(N-tert-butoxycarbonyl)-2-N-alkylamino-acetaldehyde (1.5 g) in 100 mL methanol, 1 equivalent of alkylamine is added. To this solution 2 equivalents of potassium carbonate is added. The solution was heated to reflux for 30 minutes. The solution was cooled in an ice bath and 2 equivalents of $NaBH_4$ were slowly added. After the addition the reaction mixture was allowed to slowly rise to room temperature and stirred for 2 hours. The reaction mixture was evaporated and the residue was partitioned between water and chloroform. The chloroform layer was separated, dried with $MgSO_4$, and the solvent was to yield the product. Yields were typically 30-40%.

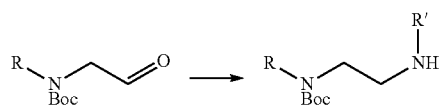

General Synthesis of N-(tert-Butoxycarbonyl)-N-Alkylamino-Alkyl Carbonyl Linked N'-(tert-Butoxycarbonyl)-Hydroxylamine To N-(tert-butoxycarbonyl)-alkylamino alcohol (N-Boc) (0.5 g) in 20 mL dichloromethane 0.35 equivalent of triphosgene is added. To this solution 1 equivalent of pyridine is added dropwise. To this solution 1 equivalent of N-Boc hydroxylamine is added followed by 1 equivalent of pyridine. The solution is stirred for five minutes and the entire reaction is filtered through a short plug of silica. The plug is washed with dichloromethane and the filtrate was evaporated. Typical yields were 90-100%.

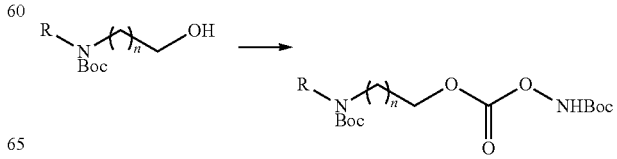

General Synthesis of N-(tert-Butoxycarbonyl)-N-Alkylamino-Ethyl Carbamoyl Linked N'-(tert-Butoxycarbonyl)-Hydroxylamine To N-Boc hydroxylamine (0.5 g) in 20 mL dichloromethane 0.35 equivalent of triphosgene is added. To this solution 1 equivalent of pyridine is added dropwise. To this solution 1 equivalent of N-(tert-butoxycarbonyl)-N-alkyl-N'-alkyl ethylene-diamine is added followed by 2 equivalents of triethylamine. The solution is stirred for five minutes and the entire reaction is washed with 10% HCl. The organic layer is separated, dried with MgSO$_4$, and evaporated.

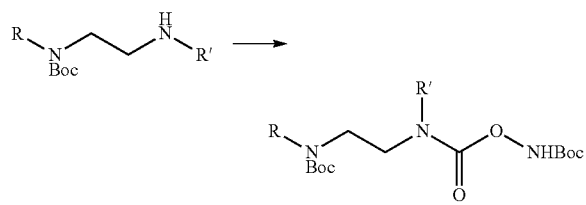

General Synthesis of N-(tert-Butoxycarbonyl)-N-Alkylamino-Alkyl (Carbonyl/Carbamoyl) Linked N'-(tert-Butoxycarbonyl)-N'-Arenesulfonamides To a solution of N-(tert-butoxycarbonyl)-N-alkylamino-alkyl (carbonyl/carbamoyl) linked N'-(tert-butoxycarbonyl)-hydroxylamine (1 g) in 20 mL dichloromethane 1 equivalent of arylsulfonyl chloride and 0.10 equivalent of DMAP is added. To this mixture 1 equivalent of triethylamine is added. The reaction is stirred until completion, which is indicated by TLC. The reaction solvent is evaporated and the crude product is purified by silica gel chromatography. It is important that the silica has been previously deactivated by triethylamine before purification. Yields are typically 60%.

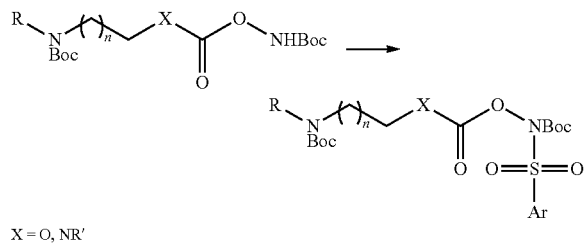

General synthesis of sulfonamidyl-alkylamino (carbamate/carbonate) hydrochlorides 1 and 2

To a solution of N-(tert-butoxycarbonyl)-N-alkylamino (carbonyl/carbamoyl) linked N'-(tert-butoxycarbonyl)-N'-arenesulfonamide (1 g) in 50 mL methanol, which is cooled in a dry ice/acetone bath, anhydrous HCl is bubbled through for twenty minutes. After bubbling, the reaction mixture is allowed to stir for two hours at room temperature. The mixture is evaporated and the resultant compound is washed several times with ether. After the washes, the salt is dried on a vacuum pump for several hours. Yields are typically 90-100%.

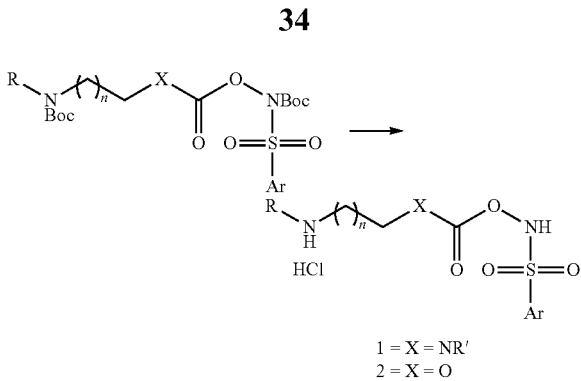

2-Bromo-benzenesulfonamidyl-2-(methylamino)-ethyl carbonate hydrochlor-ide (5a)

$^1$H NMR (400 MHz, δ) 2.53 (3H, s), 3.21 (2H, t), 4.44 (2H, t), 7.66 (2H, m), 7.92 (1H, d), 7.98 (1H, d), 9.09 (2H, brs), 12.11 (1H, brs); $^{13}$C NMR (100 MHz, δ) 32.62, 46.38, 65.10, 120.17, 128.45, 131.52, 135.47, 135.91, 136.29, 152.91; FAB-MS 352.98093 (M+H $^{79}$Br) (352.98068 cal.), 354.97905 (M+H $^{81}$Br) (354.97863 cal.)

2-Bromo-benzenesulfonamidyl-2-(benzylamino)-ethyl carbonate hydrochlori-de (5b)

$^1$H NMR (400 MHz, δ) 2.02 (2H, m), 2.93 (2H, m), 4.11 (2H, t), 4.26 (2H, t), 7.41-7.56 (5H, m), 7.66 (2H, m), 7.92 (1H, d), 8.01 (1H, d), 9.43 (2H, brs), 12.05 (1H, brs); $^{13}$C NMR (100 MHz, δ) 24.72, 43.23, 49.93, 120.16, 128.46, 128.63, 128.90, 130.06, 131.50, 132.00, 135.43, 135.87, 136.25, 153.10; FAB-MS 429.01181 (M+H $^{79}$Br) (429.01198 cal.), 431.00911 (M+H $^{81}$Br) (431.00993 cal.)

2-Bromo-benzenesulfonamidyl-2-(iso-propylamino)-ethyl carbonate hydroc-hloride (5c)

$^1$H NMR (400 MHz, δ) 1.22 (6H, d), 3.20 (1H, m) 3.20 (2H, m) 4.48 (2H, t) 7.66 (2H, m), 7.92 (1H, d), 8.05 (1H, d), 9.25 (2H, brs), 12.26 (1H, brs); $^{13}$C NMR (100 MHz, δ) 18.86, 42.63, 50.35, 65.67, 120.57, 128.87, 131.93, 135.86, 136.30, 136.78, 153.33; FAB-MS 381.01203 (M+H $^{79}$Br) (381.01198 cal.), 383.00981 (M+H $^{81}$Br) (383.00993 cal.)

2-Bromo-benzenesulfonamidyl-2-(tert-butylamino)-ethyl carbonate hydrochl-oride (5d)

$^1$H NMR (400 MHz, δ) 1.26 (9H, s), 3.16 (2H, brs), 4.49 (2H, t), 7.64 (2H, m), 7.91 (1H, d), 8.06 (1H, d), 9.31 (2H, brs), 12.28 (1H, brs); $^{13}$C NMR (100 MHz, δ) 24.89, 56.48, 65.25, 120.11, 128.39, 131.47, 135.37, 135.82, 136.34, 152.87; FAB-MS 395.02744 (M+H $^{79}$Br) (395.02763 cal.), 397.02573 (M+H $^{81}$Br) (397.02558 cal.)

2-Bromo-benzenesulfonamidyl-2-(phenylamino)-ethyl carbonate hydrochlo-ride (5e)

$^1$H NMR (400 MHz, δ) 3.52 (2H, t), 4.43 (2H, t), 7.20-7.36 (5H, m), 7.64 (2H, m), 7.91 (1H, d), 8.04 (1H, d), 9.90 (2H, brs), 12.13 (1H, brs); $^{13}$C NMR (100 MHz, δ) 64.96, 65.71, 118.01, 119.79, 120.16, 128.43, 128.91, 129.64, 131.57, 135.41, 135.86, 136.30, 153.05; FAB-MS 414.99567 (M+H $^{79}$Br) (414.99633 cal.), 416.99335 (M+H $^{81}$Br) (416.99428 cal.)

2-Bromo-benzenesulfonamidyl-2-(4-methoxy-phenylamino)-ethyl carbonate hydrochloride (5f)

$^1$H NMR (400 MHz, δ) 3.54 (2H, t), 3.76 (3H, s), 4.46 (2H, t), 7.01 (2H, m), 7.37 (2H, m), 7.66 (2H, m), 7.93 (1H, d), 8.04 (1H, d); $^{13}$C NMR (100 MHz, δ) 55.51, 61.35, 64.98, 114.05, 114.95, 119.99, 120.17, 128.41, 131.55, 131.75, 135.42, 135.87, 136.28, 152.89; FAB-MS 445.00601 (M+H $^{79}$Br) (445.00684 cal.), 447.00464 (M+H $^{81}$Br) (447.00485 cal.)

2-Bromo-benzenesulfonamidyl-2-(4-chloro-phenylamino)-ethyl carbonate hydrochloride (5g)

$^1$H NMR (400 MHz, δ) 3.35 (2H, t), 4.31 (2H, 5), 6.80 (2H, m), 7.18 (2H, m), 7.63 (2H, m), 7.90 (1H, d), 8.01 (1H, d), 8.90 (2H, brs), 12.04 (1H, brs); $^{13}$C NMR (100 MHz, δ) 65.01, 67.40, 120.17, 122.30, 128.43, 128.94, 129.71, 131.56, 135.41, 135.87, 136.30, 153.28; FAB-MS 447.95076 (M+H $^{35}$Cl$^{79}$Br) (447.94953 cal.)

2-Bromo-benzenesulfonamidyl-3-(iso-propylamino)-propyl carbonate hydro-chloride (5h)

$^1$H NMR (400 MHz, δ) 1.21 (6H, m), 2.01 (2H, brs), 2.89 (2H, brs), 3.22 (1H, brs), 4.27 (2H, brs), 7.64 (2H, m), 7.90 (1H, m), 8.04 (1H, m), 9.14 (2H, brs), 12.14 (1H, brs); $^{13}$C NMR (100 MHz, δ) 18.48, 25.00, 40.49, 49.40, 66.97, 120.15, 128.44, 131.50, 135.39, 135.82, 136.23, 153.12; FAB-MS 395.02704 (M+H $^{79}$Br) (395.02763 cal.), 397.02519 (M+H $^{81}$Br) (397.02558 cal.)

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Saari, W. S.; Schwering, J. E.; Lyle, P. A.; Smith, S. J.; Engelhardt, E. L. *J. Med. Chem.* 1990, 33, 97-101.

Thomsen, K. F.; Strom, F.; Sforzini, B. V.; Begtrup, M.; Mork, N. *Int. J. Pharm.* 1994, 112, 143-152.

Toscano, J. P.; Brookfield, F. A.; Cohen, A. D.; Courtney, S. M.; Frost, L. M.; Kalish, V. J. In U.S. Pat. No. 8,030,356, 2011.

Kato, S.; Harada, H.; Morie, T. *J. Chem. Soc., Perkin Trans.* 1 1997, 3219-3226.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

(I)

or a pharmaceutically acceptable salt thereof, wherein:
n is an integer selected from the group consisting of 1, 2, and 3;
$X_1$ is selected from the group consisting of O and $NR_1$;
R and $R_1$ are each independently selected from the group consisting of H, unsubstituted or substituted linear alkyl, unsubstituted or substituted branched alkyl, and unsubstituted or substituted aryl;
$X_2$ is a leaving group selected from the group consisting of halogen and L-Y;
L is a bond, —$SO_2$—, or —O—;
Y is W, alkyl, monocyclic cycloalkyl, bicyclic cycloalkyl, tricyclic cycloalkyl, heterocycloalkyl, aryl, or heteroaryl, each of which are unsubstituted or substituted with one or more substituent groups selected from W;
W is a substituent group selected from the group consisting of unsubstituted or substituted linear alkyl, unsubstituted or substituted branched alkyl, alkoxyl, perhaloalkyl, hydroxyl, hydroxyalkyl, alkylsulfonyl, alkylsulfanyl, alkylsulfinyl, N-hydroxylsulfonamidyl, carboxyl, carbonyl, carbamoyl, alkylcarbamoyl, halogen, amino, dialkylamino, cycloalkoxyl, cycloalkylsulfanyl, arylsulfanyl, arylsulfinyl, nitro, nitrile, amide, haloalkyl, unsubstituted or substituted heterocycloalkyl, unsubstituted or substituted aryl, unsubstituted or substituted aryloxyl, cycloalkyl, aralkyloxyl, —$SO_3H$, acyl, —$COR_2$, —$COOR_2$, —$CONR_2R_3$, —$CH(C(O)R_2)_2$, —$SO_2R_2$, and —$COX_3$;
$X_3$ is halogen; and
$R_2$ and $R_3$ are independently unsubstituted alkyl or aryl, or $R_2$ and $R_3$ are taken together to form an unsubstituted or substituted cycloalkyl or an unsubstituted or substituted heterocycloalkyl.

2. The compound of claim 1 or a pharmaceutically acceptable salt thereof, wherein the compound of formula (I) has the following structure:

wherein:
m is an integer selected from the group consisting of 0, 1, 2, 3, 4, and 5; and
each $Y_1$ is independently selected from the group consisting of unsubstituted or substituted linear alkyl, unsubstituted or substituted branched alkyl, alkoxyl, perhaloalkyl, hydroxyl, hydroxyalkyl, alkylsulfonyl, alkylsulfanyl, alkylsulfinyl, N-hydroxylsulfonamidyl, carboxyl, carbonyl, carbamoyl, alkylcarbamoyl, halogen, amino, dialkylamino, cycloalkoxyl, cycloalkylsulfanyl, arylsulfanyl, arylsulfinyl, nitro, nitrile, amide, haloalkyl, unsubstituted or substituted heterocycloalkyl, unsubstituted or substituted aryl, unsubstituted or substituted aryloxyl, cycloalkyl, aralkyloxyl, —SO₃H, and acyl.

3. The compound of claim 2 or a pharmaceutically acceptable salt thereof, wherein the compound of formula (I) has the following structure:

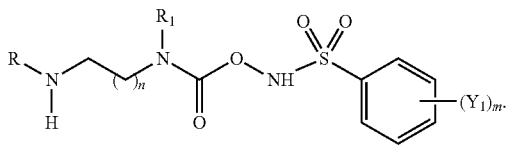

4. The compound of claim 3 or a pharmaceutically acceptable salt thereof, wherein R is selected from the group consisting of methyl, iso-propyl, benzyl, and phenyl.

5. The compound of claim 3 or a pharmaceutically acceptable salt thereof, wherein $R_1$ is selected from the group consisting of methyl, ethyl, sec-butyl, and benzyl.

6. The compound of claim 3 or a pharmaceutically acceptable salt thereof, wherein n is 1 or 2.

7. The compound of claim 3 or a pharmaceutically acceptable salt thereof, wherein n is 1.

8. The compound of claim 2 or a pharmaceutically acceptable salt thereof, wherein the compound of formula (I) has the following structure:

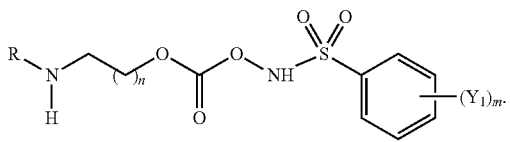

9. The compound of claim 8 or a pharmaceutically acceptable salt thereof, wherein R is selected from the group consisting of methyl, iso-propyl, tert-butyl, benzyl, phenyl, 4-chlorophenyl, and 4-methoxyphenol.

10. The compound of claim 2 or a pharmaceutically acceptable salt thereof, wherein n is 1 or 2.

11. The compound of claim 2 or a pharmaceutically acceptable salt thereof, wherein n is 1.

12. The compound of claim 1 or a pharmaceutically acceptable salt thereof, wherein n is 1 or 2.

13. The compound of claim 1 or a pharmaceutically acceptable salt thereof, wherein n is 1.

14. A pharmaceutical composition comprising a compound of claim 1 or a pharmaceutically acceptable salt thereof, and a pharmaceutically acceptable carrier.

15. A kit comprising a compound of claim 1 or a pharmaceutically acceptable salt thereof.

16. The kit of claim 15, further comprising instructions for use in treating a disease or condition that is responsive to nitroxyl therapy.

17. A compound of the structure

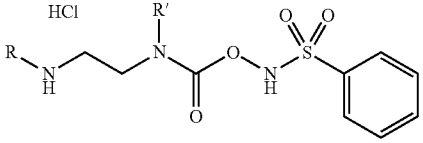

or a pharmaceutically acceptable salt thereof wherein:
R is methyl and R' is methyl;
R is benzyl and R' is methyl;
R is iso-propyl and R' is methyl;
R is phenyl and R' is methyl;
R is methyl and R' is ethyl;
R is methyl and R' is benzyl; or
R is methyl and R' is sec-butyl.

18. A compound which is:
2-bromo-benzenesulfonamidyl-2-(methylamino)-ethyl carbonate hydrochloride;
2-bromo-benzenesulfonamidyl-2-(benzylamino)-ethyl carbonate hydrochloride;
2-bromo-benzenesulfonamidyl-2-(iso-propylamino)-ethyl carbonate hydrochloride;
2-bromo-benzenesulfonamidyl-2-(tert-butylamino)-ethyl carbonate hydrochloride;
2-bromo-benzenesulfonamidyl-2-(phenylamino)-ethyl carbonate hydrochloride;
2-bromo-benzenesulfonamidyl-2-(4-methoxy-phenylamino)-ethyl carbonate hydrochloride;
2-bromo-benzenesulfonamidyl-2-(4-chloro-phenylamino)-ethyl carbonate hydrochloride;
2-bromo-benzenesulfonamidyl-3-(iso-propylamino)-propyl carbonate hydrochloride; or
a pharmaceutically acceptable salt thereof.

* * * * *